(12) United States Patent
Assmann et al.

(10) Patent No.: US 6,384,066 B1
(45) Date of Patent: May 7, 2002

(54) SULPHONYLTRIAZOL DERIVATIVES AND THEIR USE FOR COMBATING MICRO-ORGANISMS

(75) Inventors: Lutz Assmann, Langenfeld; Stefan Hillebrand, Neuss; Klaus Stenzel, Düsseldorf; Ulrike Wachendorff-Neumann, Neuwied, all of (DE)

(73) Assignee: Bayer Aktiengesellschaft, Leverkusen (DE)

( * ) Notice: Subject to any disclaimer, the term of this patent is extended or adjusted under 35 U.S.C. 154(b) by 0 days.

(21) Appl. No.: 09/787,650
(22) PCT Filed: Sep. 20, 1999
(86) PCT No.: PCT/EP99/06938
  § 371 Date: Mar. 20, 2001
  § 102(e) Date: Mar. 20, 2001
(87) PCT Pub. No.: WO00/18742
  PCT Pub. Date: Apr. 6, 2000

(30) Foreign Application Priority Data

Sep. 29, 1998 (DE) .......................................... 198 44 497

(51) Int. Cl.⁷ ........................ A07N 43/80; C07D 413/12
(52) U.S. Cl. ........................ 514/380; 548/243; 548/244
(58) Field of Search ........................ 514/380; 548/243, 548/244

(56) References Cited

U.S. PATENT DOCUMENTS

| 4,734,427 A | 3/1988 | Riebel et al. ............... 514/398 |
| 5,985,903 A | 11/1999 | Assmann et al. ........... 514/359 |
| 6,043,377 A | 3/2000 | Assmann et al. ........... 548/243 |
| 6,172,092 B1 | 1/2001 | Assmann et al. ........... 514/359 |

FOREIGN PATENT DOCUMENTS

| EP | 284277 | * 9/1988 |
| JP | 2-174758 | * 6/1990 |
| WO | 99/02518 | 1/1999 |

OTHER PUBLICATIONS

Cram and Hammond, "Organic Chemistry", Mc–Graw Hill Book Co., New York, (1964), 2nd ed., pp. 565–567.*

J. Parkt. Chem. 312, (month unavailable) 1970, pp. 610–612, Von H.G.O. Becker, G. Görmar and H.–J.. Timpe, Darstellung und Reaktionen von 4–Hydroxy–1,2,4–triazolen.

J. Heterocyclic Chem. Aug. 1981, pp. 997–1006, Richard J. Cremlyn, Fred. J Swinbourne & Kin–Man Yung, Some Heterocyclic Sulfonyl Chlorides and Derivatives.

* cited by examiner

Primary Examiner—Patricia L. Morris
(74) Attorney, Agent, or Firm—Joseph C. Gil

(57) ABSTRACT

Novel sulphonyltriazole derivatives of the formula

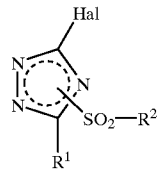

(I)

in which

Hal represents fluorine, chlorine or bromine, $R^1$ represents hydrogen, alkyl, alkoxyalkyl, cycloalkyl, alkylaminocarbonyl, optionally substituted phenyl, optionally substituted phenoxy or represents optionally substituted heterocyclyl and $R^2$ represents alkyl or represents optionally substituted heterocyclyl or represents a radical of the formula

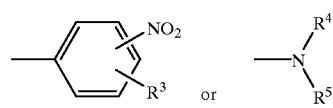

in which $R^3$ represents halogen, alkyl or phenyl, $R^4$ represents hydrogen or alkyl and $R^5$ represents alkyl or optionally substituted phenyl, or $R^4$ and $R^5$ together with the nitrogen atom to which they are attached form a heterocyclic ring which may be substituted and which may also contain an additional heteroatom, a process for preparing these substances and their use for controlling undesirable microorganisms.

9 Claims, No Drawings

SULPHONYLTRIAZOL DERIVATIVES AND THEIR USE FOR COMBATING MICROORGANISMS

This application is a 371 of PCT/EP99/06938 filed Sep. 20, 1999.

The present invention relates to novel sulphonyltriazole derivatives, to a process for their preparation and to their use for controlling undesirable microorganisms.

It is already known that certain benzotriazole derivatives have fungicidal properties (cf. DE-A 195 23 446). Thus, for example, 1-(3,5-dimethyl-isoxazole4-sulphonyl)-1H-benzotriazole can be used for controlling fungi. The activity of this substance is good; however, it is sometimes unsatisfactory at low application rates.

This invention, accordingly, provides novel sulphonyltriazole derivatives of the formula

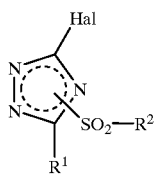

(I)

in which

Hal represents fluorine, chlorine or bromine, $R^1$ represents hydrogen, alkyl, alkoxyalkyl, cycloalkyl, alkylaminocarbonyl, optionally substituted phenyl, optionally substituted phenoxy or represents optionally substituted heterocyclyl and $R^2$ represents alkyl or represents optionally substituted heterocyclyl or represents a radical of the formula

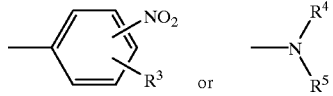 or 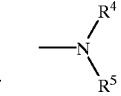

in which $R^3$ represents halogen, alkyl or phenyl, $R^4$ represents hydrogen or alkyl and $R^5$ represents alkyl or optionally substituted phenyl, or $R^4$ and $R^5$ together with the nitrogen atom to which they are attached form a heterocyclic ring which may be substituted and may also contain an additional heteroatom.

Furthermore, it has been found that sulphonyltriazole derivatives of the formula (I) are obtained when triazoles of the formula

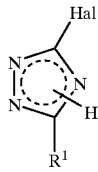

(II)

in which $R^1$ and Hal are as defined above, are reacted with sulphonyl halides of the formula $$R^2\text{—}SO_2\text{—}Hal^1 \qquad (III)$$

in which $R^2$ is as defined above and $Hal^1$ represents chlorine or bromine, if appropriate in the presence of an acid binder and if appropriate in the presence of a diluent.

Finally, it has been found that the sulphonyltriazole derivatives of the formula (I) have very good microbicidal properties and can be used for controlling undesirable microorganisms in crop protection and in agriculture.

Surprisingly, the sulphonyltriazole derivatives of the formula (I) according to the invention have considerably better fungicidal activity than 1-(3,5-dimethyl-isoxazole-4-sulphonyl)-1H-benzotriazole, which is a known active compound of the same direction of action and of similar constitution.

The sulphonyltriazole derivatives according to the invention are in each case defined substances; however, their structure cannot always be defined unambiguously. They can be present as compounds of one of the formulae

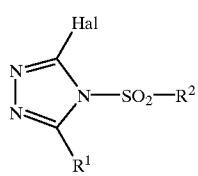

(Ia)

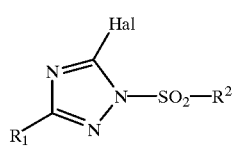

(Ib)

or

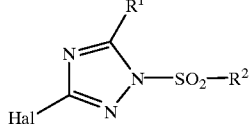

(Ic)

or else as isomer mixtures.

The notation chosen for the formula (I) is meant to indicate that the positions of the double bonds in the triazole ring and the point of attachment of the —SO$_2$—R$^2$ group cannot always be determined unambiguously.

The formula (I) provides a general definition of the substances according to the invention.

Hal also preferably represents fluorine, chlorine or bromine.

$R^1$ preferably represents hydrogen, alkyl having 1 to 6 carbon atoms, alkoxyalkyl having 1 to 6 carbon atoms in the alkoy moiety and 1 to 6 carbon atoms in the alkyl moiety, cycloalkyl having 3 to 8 carbon atoms or represents alkylaminocarbonyl having 1 to 6 carbon atoms in the alkyl moiety, or $R^1$ represents phenyl which may be mono- to trisubstituted by identical or different substituents from the group consisting of halogen, nitro, $C_1$–$C_6$-alkyl, $C_1$–$C_6$-alkoxy, $C_1$–$C_6$-alkylthio, $C_1$–$C_6$-halogenoalkyl having 1 to 5 identical or different halogen atoms, $C_1$–$C_6$-halogenoalkoxy having 1 to 5 identical or different halogen atoms, $C_1$–$C_6$-halogenalkylthio having 1 to 5 identical or different halogen atoms, cyano and cycloalkyl having 3 to 6 carbon atoms, or $R^1$ represents phenoxy which may be mono- to trisubstituted by identical or different substituents from the group consisting of halogen, nitro, $C_1$–$C_6$-alkyl, $C_1$–$C_6$-alkoxy, $C_1$–$C_6$-alkylthio, $C_1$–$C_6$-halogenoalkyl having 1 to 5 identical or different halogen atoms, $C_1$–$C_6$-halogenoalkoxy having 1 to 5 identical or different halogen atoms, $C_1$–$C_6$-halogenoalkylthio having 1 to 5 identical or different halogen atoms, cyano and cycloalkyl having 3 to 6 carbon atoms, or $R^1$ represents a heterocyclyl radical having 5 or 6 ring members and 1 to 3 heteroatoms, such as nitrogen, oxygen and/or sulphur, where this radical may be mono- to trisubstituted by identical or different substituents from the group consisting of halogen, cyano, nitro, amino, hydroxyl, alkyl having 1 to 4 carbon atoms, alkoxy having 1 to 4 carbon atoms, halogenoalkyl having 1 to 4 carbon atoms and 1 to 5 identical or different halogen atoms, halogenoalkoxy having 1 to 4 carbon atoms and 1 to 5 identical or different halogen atoms, alkylcarbonyl having 1 to 4 carbon atoms in the alkyl moiety, alkoxycarbonyl having 1 to 3 carbon atoms in the alkoxy moiety, carbamoyl, alkylaminocarbonyl having 1 to 4 carbon atoms in the alkyl moiety, dialkylaminocarbonyl having 1 to 4 carbon atoms in the individual alkyl moieties, hydroximinoalkyl or alkoximinoalkyl having in each case 1 to 4 carbon atoms in the individual alkyl moieties and cycloalkyl having 3 to 6 carbon atoms.

$R^2$ preferably represents alkyl having 1 to 6 carbon atoms or represents a heterocyclyl radical having 5 or 6 ring members and 1 to 3 heteroatoms, such as nitrogen, oxygen and/or sulphur, where this radical may be mono- to trisubstituted by identical or different substituents from the group consisting of halogen, cyano, nitro, amino, hydroxyl, alkyl having 1 to 4 carbon atoms, alkoxy having 1 to 4 carbon atoms, halogenoalkyl having 1 to 4 carbon atoms and 1 to 5 identical or different carbon atoms, halogenoalkoxy having 1 to 4 carbon atoms and 1 to 5 identical or different halogen atoms, alkylcarbonyl having 1 to 4 carbon atoms in the alkyl moiety, alkoxycarbonyl having 1 to 3 carbon atoms in the alkoxy moiety, carbamoyl, alkylaminocarbonyl having 1 to 4 carbon atoms in the alkyl moiety, dialkylaminocarbonyl having 1 to 4 carbon atoms in the individual alkyl moieties, hydroximinoalkyl or alkoximinoalkyl having in each case 1 to 4 carbon atoms in the individual alkyl moieties or cycloalkyl having 3 to 6 carbon atoms.

$R^2$ furthermore preferably represents a radical of the formula

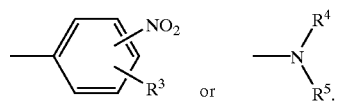

$R^3$ preferably represents fluorine, chlorine, bromine, alkyl having 1 to 6 carbon atoms or represents phenyl.

$R^4$ preferably represents hydrogen or alkyl having 1 to 6 carbon atoms.

$R^5$ preferably represents alkyl having 1 to 6 carbon atoms or represents phenyl which may be mono- to trisubstituted by identical or different substituents from the group consisting of halogen, nitro, $C_1$–$C_6$-alkyl, $C_1$–$C_6$-alkoxy, $C_1$–$C_6$-alkylthio, $C_1$–$C_6$-halogenoalkyl having 1 to 5 identical or different halogen atoms, $C_1$–$C_6$-halogenoalkoxy having 1 to 5 identical or different halogen atoms, $C_1$–$C_6$-halogeno-alkylthio having 1 to 5 identical or different halogen atoms, cyano and cycloalkyl having 3 to 6 carbon atoms.

$R^4$ and $R^5$ furthermore also together with the nitrogen atom to which they are attached preferably represent a saturated heterocyclic ring having 5 or 6 ring members, where the ring may contain a further nitrogen or oxygen atom and may be mono- to tetrasubstituted by identical or different substituents from the group consisting of halogen and alkyl having 1 to 4 carbon atoms.

Hal also particularly preferably represents fluorine, chlorine or bromine.

$R^1$ particularly preferably represents hydrogen, methyl, ethyl, n-propyl, iso-propyl, n-butyl, sec-butyl, iso-butyl or tert-butyl, represents alkoxyalkyl having 1 to 4 carbon atoms in the alkoxy moiety and 1 to 4 carbon atoms in the alkyl moiety, represents cycloalkyl having 3 to 7 carbon atoms or represents alkylaminocarbonyl having 1 to 4 carbon atoms in the alkyl moiety, or $R^1$ particularly preferably represents phenyl which may be mono- to trisubstituted by identical or different substituents from the group consisting of fluorine, chlorine, bromine, nitro, methyl, ethyl, n- or i-propyl, n-, i-, s- or t-butyl, methoxy, ethoxy, n- or i-propoxy, methylthio, ethylthio, n- or i-propylthio, trifluoromethyl, trifluoroethyl, difluoromethoxy, trifluoromethoxy, difluorochloromethoxy, trifluoroethoxy, cyano, cyclopropyl, cyclopentyl and cyclohexyl, or $R^1$ particularly preferably represents phenoxy which may be mono- to trisubstituted by identical or different substituents from the group consisting of fluorine, chlorine, bromine, nitro, methyl, ethyl, n- or i-propyl, n-, i-, s- or t-butyl, methoxy, ethoxy, n- or i-propoxy, methylthio, ethylthio, n- or i-propylthio, trifluoromethyl, trifluoroethyl, difluoromethoxy, trifluoromethoxy, difluorochloromethoxy, trifluoroethoxy, cyano, cyclopropyl, cyclopentyl and cyclohexyl, $R^1$ furthermore particularly preferably represents furyl, thienyl, oxazolyl, isoxazolyl, pyrazolyl, imidazolyl, thiazolyl, isothiazolyl, oxadiazolyl, thiadiazolyl, pyridinyl, pyridazinyl, pyrazinyl, 1,2,3-triazinyl, 1,2,4-triazinyl, 1,3,5-triazinyl, pyrrolidinyl, piperidinyl or morpholinyl, where these heterocyclic radicals may be mono-, di- or trisubstituted by identical or different substituents from the group consisting of fluorine, chlorine, bromine, cyano, nitro, amino, hydroxyl, carbamoyl, methyl, ethyl, n- or i-propyl, n-, i-, s-, or t-butyl, cyclopropyl, methoxy, ethoxy, n- or i-propoxy, trifluoromethyl, trifluoroethyl, difluoromethoxy, trifluoromethoxy, acetyl, propionyl, methoxycarbonyl, ethoxycarbonyl, hydroximinomethyl, hydroximinoethyl, methoximinomethyl, ethoximinomethyl, methoximinoethyl and ethoximinoethyl.

$R^2$ particularly preferably represents methyl, ethyl, n-propyl or isopropyl or furyl, thienyl, oxazolyl, isoxazolyl, pyrazolyl, imidazolyl, thiazolyl, isothiazolyl, oxadiazolyl, thiadiazolyl, pyridinyl, pyridazinyl, pyrazinyl, 1,2,3-triazinyl, 1,2,4-triazinyl, 1,3,5-triazinyl, pyrrolidinyl, piperidinyl or morpholinyl, where these heterocyclic radicals may be mono-,. di- or trisubstituted by identical or different substituents from the group consisting of fluorine, chlorine, bromine, cyano, nitro, amino, hydroxyl, carbamoyl, methyl, ethyl, n- or i-propyl, n-, i-, s-, or t-butyl, cyclopropyl, methoxy, ethoxy, n- or i-propoxy, trifluoromethyl, trifluoroethyl, difluoromethoxy, trifluoromethoxy, acetyl, propionyl, methoxycarbonyl, ethoxycarbonyl, hydroximinomethyl, hydroxyiminoethyl, methoximinomethyl, ethoximinomethyl, methoximinoethyl and ethoximinoethyl.

$R^2$ furthermore particularly preferably represents a radical of the formula

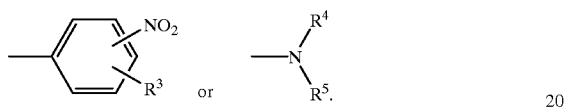

$R^3$ particularly represents fluorine, chlorine, bromine, methyl, ethyl, n-propyl, isopropyl, n-butyl, sec-butyl, iso-butyl, tert-butyl or phenyl.

$R^4$ particularly preferably represents hydrogen, methyl, ethyl, n-propyl, isopropyl, n-butyl, sec-butyl, iso-butyl or ten-butyl.

$R^5$ particularly preferably represents methyl, ethyl, n-propyl, isopropyl, n-butyl, sec-butyl, iso-butyl or tert-butyl, or represents phenyl which may be mono- to trisubstituted by identical or different substituents from the group consisting of fluorine, chlorine, bromine, nitro, methyl, ethyl, n- or i-propyl, n-, i-, s- or t-butyl, methoxy, ethoxy, n- or i-propoxy, methylthio, ethylthio, n- or i-propylthio, trifluoromethyl, trifluoroethyl, difluoromethoxy, trifluoromethoxy, difluorochloromethoxy, trifluoroethoxy, cyano, cyclopropyl, cyclopentyl and cyclohexyl.

$R^4$ and $R^5$ furthermore also together with the nitrogen atom to which they are attached particularly preferably represent pyrrolidinyl, piperidinyl, morpholinyl or piperazinyl, where each of these radicals may be mono- to tetrasubstituted by identical or different substituents from the group consisting of fluorine, chlorine, bromine, methyl, ethyl, n-propyl, isopropyl, n-butyl, i-butyl, sec-butyl or tert-butyl.

Hal very particularly preferably represents chlorine or bromine.

$R^1$ very particularly preferably represents hydrogen, methyl, ethyl, n-propyl, isopropyl, n-butyl, sec-butyl, iso-butyl or tert-butyl, represents alkoyalkyl having 1 or 2 carbon atoms in the alkoxy moiety and 1 or 2 carbon atoms in the alkyl moiety, represents cyclopropyl, cyclopentyl, cyclohexyl or represents alkylaminocarbonyl having 1 to 4 carbon atoms in the alkyl moiety, or $R^1$ very particularly preferably represents phenyl which may be mono- to trisubstituted by identical or different substituents from the group consisting of fluorine, chlorine, bromine, nitro, methyl, ethyl, n- or i-propyl, n-, i-, s- or t-butyl, methoxy, ethoxy, n- or i-propoxy, methylthio, ethylthio, n- or i-propylthio, trifluoromethyl, trifluoroethyl, difluoromethoxy, trifluoromethoxy, difluorochloromethoxy, trifluoroethoxy, cyano, cyclopropyl, cyclopentyl and cyclohexyl, or $R^1$ very particularly preferably represents phenoxy which may be mono- to trisubstituted by identical or different substituents from the group consisting of fluorine, chlorine, bromine, nitro, methyl, ethyl, n - or i-propyl, n-, i-, s- or t-butyl, methoxy, ethoxy, n- or i-propoxy, methylthio, ethylthio, n- or i-propylthio, trifluoromethyl, trifluoroethyl, difluoromethoxy, trifluoromethoxy, difluorochloromethoxy, trifluoroethoxy, cyano, cyclopropyl, cyclopentyl and cyclohexyl, $R^1$ furthermore very particularly preferably represents furyl, thienyl, oxazolyl, isoxazolyl, pyrazolyl, imidazolyl, thiazolyl, isothiazolyl, oxadiazolyl, thiadiazolyl, pyridinyl, 1,2,4-triazinyl, pyrrolidinyl, piperidinyl or morpholinyl, where these heterocyclic radicals may be mono-, di- or trisubstituted by identical or different substituents from the group consisting of fluorine, chlorine, bromine, cyano, amino, hydroxyl, carbamoyl, methyl, ethyl, n- or i-propyl, cyclopropyl, methoxy, ethoxy, Trifluoromethyl, difluoromethoxy, trifluoromethoxy, acetyl, methoxycarbonyl, ethoxycarbonyl, hydroximinomethyl, hydroximinoethyl, methoximinomethyl, ethoximinomethyl, methoximinoethyl and ethoximinoethyl.

$R^2$ very particularly preferably represents methyl, ethyl, n-propyl or isopropyl or represents furyl, thienyl, oxazolyl, isoxazolyl, pyrazolyl, imidazolyl, thiazolyl, isothiazolyl, oxadiazolyl, thiadiazolyl, pyridinyl, 1,2,4-triazinyl, pyrrolidinyl, piperidinyl or morpholinyl, where these heterocyclic radicals may be mono- di- or trisubstituted by identical or different substituents from the group consisting of fluorine, chlorine, bromine, cyano, nitro, amino, hydroxyl, carbamoyl, methyl, ethyl, n- or i-propyl, cyclopropyl, methoxy, ethoxy, trifluoromethyl, difluoromethoxy, trifluoromethoxy, acetyl, methoxycarbonyl, ethoxycarbonyl, hydroximinomethyl, hydroximinoethyl, methoximinomethyl, ethoximinomethyl, methoximinoethyl and ethoximinoethyl.

$R^2$ furthermore very particularly preferably represents a radical of the formula

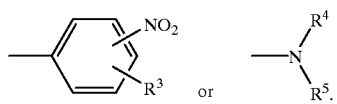

$R^3$ very particularly preferably represents fluorine, chlorine, bromine, methyl, ethyl, n-propyl, isopropyl, n-butyl, tert-butyl or phenyl.

$R^4$ very particularly preferably represents hydrogen, methyl, ethyl, n-propyl, isopropyl or n-butyl.

$R^5$ very particularly preferably represents methyl, ethyl, n-propyl, isopropyl, n-butyl, sec-butyl, iso-butyl or tert-butyl, or represents phenyl which may be mono- to trisubstituted by identical or different substituents from the group consisting of fluorine, chlorine, bromine, nitro, methyl, ethyl, n- or i-propyl, n-, i-, s- or t-butyl, methoxy, ethoxy, methylthio, trifluoromethyl, trifluoroethyl, difluoromethoxy, trifluoromethoxy, difluorochloromethoxy, trifluoroethoxy, cyano, cyclopropyl, cyclopentyl and cyclohexyl.

$R^4$ and $R^5$ furthermore also together with the nitrogen atom to which they are attached very particularly preferably represent pyrrolidinyl, piperidinyl, morpholinyl or piperazinyl, where each of these radicals may be mono- to tetrasubstituted by identical or different substituents from the group consisting of fluorine, chlorine, methyl and ethyl.

The meanings of the substituents given above can be combined with one another as desired. Moreover, individual definitions may not apply.

If 3-phenyl-5-chloro-1,2,4-triazole and 3,5-dimethyl-isoxazole 4-sulphonyl chloride are used as starting materials, the course of the process according to the invention can be illustrated by the following equation:

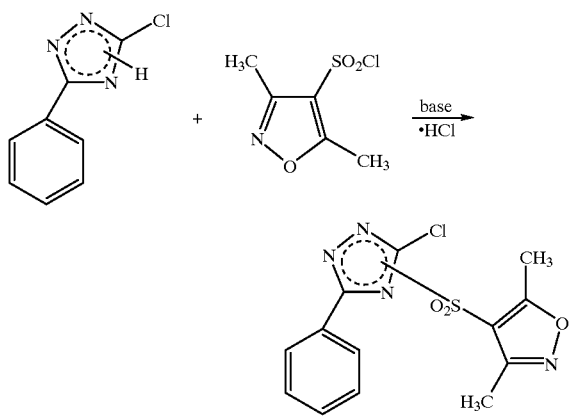

The formula (II) provides a general definition of the triazoles required as starting materials for carrying out the process according to the invention. In this formula, $R^1$ and Hal preferably have those meanings which have already been mentioned in connection with the description of the substances of the formula (I) according to the invention as being preferred for these radicals.

The triazoles of the formula (II) can be present in the three following tautomeric forms.

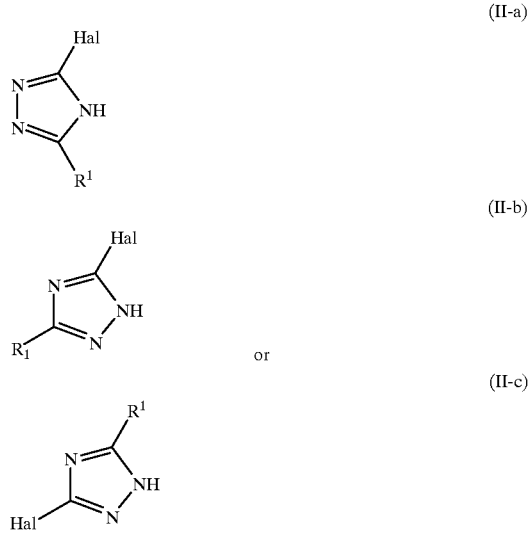

Thus, in the reaction according to the invention with sulphonyl halides of the formula (III), end products of the formula (I) can be formed which are derived from the tautomeric forms of the formulae (IIa), (IIb) and/or (IIc). If a plurality of tautomers reacts, end products of the formula (I) are obtained in the form of mixtures.

The triazoles of the formula (II) are known or can be prepared by known methods (cf. J. prakt. Chem. 312 (1970), 610–621).

The formula (III) provides a general definition of the sulphonyl halides required as reaction components for carrying out the process according to the invention. In this formula, $R^2$ preferably has that meaning which has already been mentioned in connection with the description of the compounds of the formula (I) according to the invention as being preferred for $R^2$. $Hal^1$ preferably represents chlorine.

The sulphonyl halides of the formula (III) are known or can be prepared by known processes (cf. J. Heterocyclic Chem. 1981, 997–1006 and EP-A 0 238 824).

Suitable diluents for carrying out the process according to the invention are all inert organic solvents. Preference is given to using aliphatic, alicyclic or aromatic hydrocarbons, such as petroleum ether, hexane, heptane, cyclohexane, methylcyclohexane, benzene, toluene, xylene or decalin; halogenated hydrocarbons, such as chlorobenzene, dichlorobenzene, dichloromethane, chloroform, carbon tetrachloride, dichloroethane or trichloroethane; ethers, such as diethyl ether, diisopropyl ether, methyl t-butyl ether, methyl t-amyl ether, dioxane, tetrahydrofuran, 1,2-dimethoxyethane, 1,2-diethoxyethane or anisole; ketones, such as acetone, butanone, methyl isobutyl ketone or cyclohexanone, nitriles, such as acetonitrile, propionitrile, n- or i-butyronitrile or benzonitrile; esters such as methyl acetate or ethyl acetate.

Suitable acid binders for carrying out the process according to the invention are all customary inorganic or organic bases. Preference is given to using alkaline earth metal or alkali metal hydrides, hydroxides, amides, alkoxides, acetates, carbonates or hydrogencarbonates, such as sodium hydride, sodium amide, sodium methoxide, sodium ethoxide, potassium tert-butoxide, sodium hydroxide, potassium hydroxide, sodium acetate, potassium acetate, calcium acetate, sodium carbonate, potassium carbonate, potassium hydrogencarbonate or sodium hydrogencarbonate, furthermore ammonium compounds, such as ammonium hydroxide, ammonium acetate or ammonium carbonate, and also tertiary amines, such as trimethylamine, triethylamine, tributylamine, N,N-dimethylaniline, N,N-dimethylbenzylamine, pyridine, N-methylpiperidine, N-methylmorpholine, N,N-dimethylaminopyridine, diazabicyclooctane (DABCO), diazabicyclononene (DBN) or diazabicycloundecene (DBU).

When carrying out the process according to the invention, the reaction temperatures can be varied within a relatively wide range. In general, the process is carried out at temperatures between 0° C. and 150° C., preferably between 10° C. and 120° C.

The process according to the invention is generally carried out under atmospheric pressure. However, it is also possible to operate under elevated or reduced pressure—in general between 0.1 bar and 10 bar.

For carrying out the process according to the invention, in general from 1 to 2 mol, preferably from 1 to 1.3 mol, of sulphonyl halide of the formula (III) and, if appropriate, from 1.0 to 2.0 mol, preferably from 1.0 to 1.3 mol, of acid acceptor are employed per mole of triazole of the formula (II).

Work-up is carried out by customary methods. In general, the reaction mixture is poured into water, the resulting mixture is extracted repeatedly with an organic solvent that is sparingly soluble in water and the combined organic phases are dried and concentrated under reduced pressure. The residue that remains can, if desired, be freed by customary purification methods of any impurities that are still present.

The compounds according to the invention have a potent microbicidal action and can be employed for controlling undesirable microorganisms, such as fungi and bacteria, in crop protection and in the protection of materials.

Fungicides are employed in crop protection for controlling Plasmodiophoromycetes, Oomycetes, Chytridiomycetes, Zygomycetes, Ascomycetes, Basidiomycetes and Deuteromycetes.

Bactericides are employed in crop protection for controlling Pseudomonadaceae, Rhizobiaceae, Enterobacteriaceae, Corynebacteriaceae and Streptomycetaceae.

Some pathogens causing fungal and bacterial diseases which come under the generic names listed above may be mentioned as examples, but not by way of limitation:

Xanthomonas species, such as, for example, *Xanthomonas campestris* pv. oryzae;

Pseudomonas species, such as, for example, *Pseudomonas syringae* pv. lachrymans;

Erwinia species, such as, for example, *Erwinia amylovora;*

Pythium species, such as, for example, *Pythium ultimum;*

Phytophthora species, such as, for example, *Phytophthora infestans;*

Pseudoperonospora species, such as, for example, *Pseudoperonospora humuli* or *Pseudoperonospora cubensis;*

Plasmopara species, such as, for example, *Plasmopara viticola;*

Bremia species, such as, for example, *Bremia lactucae;*

Peronospora species, such as, for example, *Peronospora pisi* or *P. brassicae;*

Erysiphe species, such as, for example, *Erysiphe graminis;*

Sphaerotheca species, such as, for example, *Sphaerotheca fuliginea;*

Podosphaera species, such as, for example, *Podosphaera leucotricha;*

Venturia species, such as, for example, *Venturia inaequalis;*

Pyrenophora species, such as, for example, *Pyrenophora teres* or *P. graminea* (conidia form: Drechslera, syn: Helminthosporium);

Cochliobolus species, such as, for example, *Cochliobolus sativus* (conidia form: Drechslera, syn: Helminthosporium);

Uromyces species, such as, for example, *Uromyces appendiculatus;*

Puccinia species, such as, for example, *Puccinia recondita;*

Sclerotinia species, such as, for example, *Sclerotinia sclerotiorum;*

Tilletia species, such as, for example, *Tilletia caries;*

Ustilago species, such as, for example, *Ustilago nuda* or *Ustilago avenae;*

Pellicularia species, such as, for example, Pellicularia sasakii;

Pyricularia species, such as, for example, *Pyricularia oryzae;*

Fusarium species, such as, for example, *Fusarium culmorum;*

Botrytis species, such as, for example, *Botrytis cinerea;*

Septoria species, such as, for example, *Septoria nodorum;*

Leptosphaeria species, such as, for example, *Leptosphaeria nodorum;*

Cercospora species, such as, for example, *Cercospora canescens;*

Alternaria species, such as, for example, *Alternaria brassicae;* and

Pseudocercosporella species, such as, for example, *Pseudocercosporella herpotrichoides.*

The fact that the active compounds are well tolerated by plants at the concentrations required for controlling plant diseases permits the treatment of aerial parts of plants, of propagation stock and seeds, and of the soil.

The active compounds according to the invention can be employed particularly successfully for controlling diseases in viticulture and fruit and vegetable growing, such as, for example, against Phytophthora species.

The active compounds according to the invention are also suitable for increasing the yield of crops. Moreover, they have reduced toxicity and are tolerated well by plants.

In the protection of materials, the compounds according to the invention can be employed for protecting industrial materials against infestation with, and destruction by, undesired microorganisms.

Industrial materials in the present context are understood as meaning non-living materials which have been prepared for use in industry. For example, industrial materials which are intended to be protected by active compounds according to the invention from microbial change or destruction can be adhesives, sizes, paper and board, textiles, leather, wood, paints and plastic articles, cooling lubricants and other materials which can be infested with, or destroyed by, microorganisms. Parts of production plants, for example cooling-water circuits, which may be adversely affected by proliferation of microorganisms may also be mentioned within the scope of the materials to be protected. Industrial materials which may be mentioned within the scope of the present invention are preferably adhesives, sizes, paper and boards, leather, wood, paints, cooling lubricants and heat-transfer liquids, particularly preferably wood.

Microorganisms capable of degrading or changing the industrial materials which may be mentioned are, for example, bacteria, fungi, yeasts, algae and slime organisms. The active compounds according to the invention preferably act against fungi, in particular moulds, wood-discolouring and wood-destroying fungi (Basidiomycetes), and against slime organisms and algae.

Microorganisms of the following genera may be mentioned as examples:

Alternaria, such as *Alternaria tenuis,*

Aspergillus, such as *Aspergillus niger,*

Chaetomium, such as *Chaetomium globosum,*

Coniophora, such as *Coniophora puetana,*

Lentinus, such as *Lentinus tigrinus,*

Penicillium, such as *Penicillium glaucum,*

Polyporus, such as *Polyporus versicolor,*

Aureobasidium, such as *Aureobasidium pullulans,*

Sclerophoma, such as *Sclerophoma pityophila,*

Trichoderma, such as *Trichoderma viride,*

Escherichia, such as *Escherichia coli,*

Pseudomonas, such as *Pseudomonas aeruginosa,* and

Staphylococcus, such as *Staphylococcus aureus.*

Depending on their particular physical and/or chemical properties, the active compounds can be converted to the customary formulations, such as solutions, emulsions, suspensions, powders, foams, pastes, granules, aerosols and microencapsulations in polymeric substances and in coating compositions for seeds, and ULV cool and warm fogging formulations.

These formulations are produced in a known manner, for example by mixing the active compounds with extenders, that is liquid solvents, liquefied gases under pressure, and/or solid carriers, optionally with the use of surfactants, that is emulsifiers and/or dispersants, and/or foam formers. If the extender used is water, it is also possible to use, for example, organic solvents as auxiliary solvents. Suitable liquid solvents are essentially: aromatics such as xylene, toluene or alkylnaphthalenes, chlorinated aromatics or chlorinated aliphatic hydrocarbons such as chlorobenzenes, chloroethylenes or methylene chloride, aliphatic hydrocarbons such as cyclohexane or paraffins, for example petroleum fractions, alcohols such as butanol or glycol and their ethers and esters, ketones such as acetone, methyl ethyl ketone, methyl isobutyl ketone or cyclohexanone, strongly polar solvents such as dimethylformamide or dimethyl sulphoxide, or else water. Liquefied gaseous extenders or carriers are to be understood as meaning those liquids which are gaseous at standard temperature and under atmospheric pressure, for example aerosol propellants such as halogenated hydrocarbons, or else butane, propane, nitrogen and carbon dioxide. Suitable solid carriers are: for example ground natural minerals such as kaolins, clays, talc, chalk, quartz, attapulgite, montmorillonite or diatomaceous earth, and ground synthetic minerals such as highly disperse silica, alumina and silicates. Suitable solid carriers for granules are: for example crushed and fractionated natural rocks such as calcite, marble, pumice, sepiolite and dolomite, or else synthetic granules of inorganic and organic meals, and granules of organic material such as sawdust, coconut shells, maize cobs and tobacco stalks. Suitable emulsifiers and/or foam formers are: for example nonionic and anionic emulsifiers, such as polyoxyethylene fatty acid esters, polyoxyethylene fatty alcohol ethers, for example alkylaryl polyglycol ethers, alkylsulphonates, alkylsulphates, arylsulphonates, or else protein hydrolysates. Suitable dispersants are: for example lignin-sulphite waste liquors and methylcellulose.

Tackifiers such as carboxymethylcellulose and natural and synthetic polymers in the form of powders, granules or latices, such as gum arabic, polyvinyl alcohol and polyvinyl acetate, or else natural phospholipids such as cephalins and lecithins and synthetic phospholipids can be used in the formulations. Other additives can be mineral and vegetable oils.

It is possible to use colourants such as inorganic pigments, for example iron oxide, titanium oxide and Prussian Blue, and organic dyestuffs such as alizarin dyestuffs, azo dyestuffs and metal phthalocyanine dyestuffs, and trace nutrients such as salts of iron, manganese, boron, copper, cobalt, molybdenum and zinc.

The formulations generally comprise between 0.1 and 95 per cent by weight of active compound, preferably between 0.5 and 90%.

The active compounds according to the invention can be used as such or in their formulations also mixed with known fungicides, bactericides, acaricides, nematicides or insecticides in order thus, for example, to widen the spectrum of action or to prevent development of resistance. In many cases, synergistic effects are achieved, i.e. the activity of the mixture exceeds the activity of the individual components.

Examples of co-components in mixtures are the following compounds:

Fungicides:

aldimorph, ampropylfos, ampropylfos-potassium, andoprim, anilazine, azaconazole, azoxystrobin, benalaxyl, benodanil, benomyl, benzamacril, benzamacril-isobutyl, bialaphos, binapacryl, bion, biphenyl, bitertanol, blasticidin-S, bromuconazole, bupirimate, buthiobate, calcium polysulphide, capsimycin, captafol, captan, carbendazim, carboxine, carvone, quinomethionate, chlobenthiazone, chlorofenazole, chloroneb, chloropicrin, chlorothalonil, chlozolinate, clozylacon, cufraneb, cymoxanil, cyproconazole, cyprodinil, cyprofuram, debacarb, dichlorophen, diclobutrazole, diclofluanid, diclomezine, dicloran, diethofencarb, difenoconazole, dimethirimol, dimethomorph, diniconazole, diniconazole-M, dinocap, diphenylamine, dipyrithione, ditalimfos, dithianon, dodemorph, dodine, drazoxolon, edifenphos, epoxiconazole, etaconazole, ethirimol, etridiazole, famoxadon, fenapanil, fenarimol, fenbuconazole, fenfuram, fenitropan, fenpiclonil, fenpropidin, fenpropimorph, fentin acetate, fentin hydroxide, ferbam, ferimzone, fluazinam, flumetover, fluoromide, fluquinconazole, flurprimidol, flusilazole, flusulfamide, flutolanil, flutriafol, folpet, fosetyl-alminium, fosetyl-sodium, fthalide, fuberidazole, furalaxyl, furametpyr, furcarbonil, furconazole, furconazole-cis, furmecyclox, guazatine, hexachlorobenzene, hexaconazole, hymexazole, imazalil, imibenconazole, iminoctadine, iminoctadine albesilate, iminoctadine triacetate, iodocarb, ipconazole, iprobenfos (IBP), iprodione, irumamycin, isoprothiolane, isovaledione, kasugamycin, kresoxim-methyl, copper preparations, such as: copper hydroxide, copper naphthenate, copper oxychloride, copper sulphate, copper oxide, oxine-copper and Bordeaux mixture, mancopper, mancozeb, maneb, meferimzone, mepanipyrim, mepronil, metalaxyl, metconazole, methasulfocarb, methfuroxam, metiram, metomeclam, metsulfovax, mildiomycin, myclobutanil, myclozolin, nickel dimethyldithiocarbamate, nitrothal-isopropyl, nuarimol, ofurace, oxadixyl, oxamocarb, oxolinic acid, oxycarboxim, oxyfenthiin, paclobutrazole, pefurazoate, penconazole, pencycuron, phosdiphen, pimaricin, piperalin, polyoxin, polyoxorim, probenazole, prochloraz, procymidone, propamocarb, propanosine-sodium, propiconazole, propineb, pyrazophos, pyrifenox, pyrimethanil, pyroquilon, pyroxyfur, quinconazole, quintozene (PCNB), quinoxyfen, sulphur and sulphur preparations, tebuconazole, tecloftalam, tecnazene, telcyclasis, tetraconazole, thiabendazole, thicyofen, thifluzamide, thiophanate-methyl, thiram, tioxymid, tolclofos-methyl, tolylfluanid, triadimefon, triadimenol, triazbutil, triazoxide, trichlamide, tricyclazole, tridemorph, triflumizole, triforine, triticonazole, uniconazole, validamycin A, vinclozolin, viniconazole, zarilamide, zineb, ziram and also
Dagger G,
OK-8705,
OK-8801,
α-(1,1-dimethylethyl)-β-(2-phenoxyethyl)-1H-1,2,4-triazole-1-ethanol,
α-(2,4-dichlorophenyl)-β-fluoro-b-propyl-1H-1,2,4-triazole-1-ethanol,
α-(2,4-dichlorophenyl)-β-methoxy-a-methyl-1H-1,2,4-triazole-1-ethanol,
α-(5-methyl-1,3-dioxan-5-yl)-β-[[4-(trifluoromethyl)-phenyl]-methylene]-1H-1,2,4-triazole-1-ethanol,
(5RS,6RS)-6-hydroxy-2,2,7,7-tetramethyl-5-(1H-1,2,4-triazol-1-yl)-3-octanone,
(E)-a-(methoxyimino)-N-methyl-2-phenoxy-phenylacetamide,
1-isopropyl {2-methyl-1-[[[1-(4-methylphenyl)-ethyl]-amino]-carbonyl]-propyl}carbamate,
1-(2,4-dichlorophenyl)-2-(1H-1,2,4-triazol-1-yl)ethanone O-(phenylmethyl)-oxime,
1-(2-methyl-1-naphthalenyl)-1H-pyrrole-2,5-dione,
1-(3,5-dichlorophenyl)-3-(2-propenyl)-2,5-pyrrolidinedione,
1-[(diiodomethyl)-sulphonyl]4-methyl-benzene,
1-[[2-(2,4-dichlorophenyl)-1,3-dioxolan-2-yl]-methyl]-1H-imidazole,
1-[[2-(4-chlorophenyl)-3-phenyloxiranyl]-methyl]-1H-1,2,4-triazole,
1-[1-[2-[(2,4-dichlorophenyl)-methoxy]-phenyl]-ethenyl]-1H-imidazole,
1-methyl-5-nonyl-2-(phenylmethyl)-3-pyrrolidinol,
2',6'-dibromo-2-methyl-4'-trifluoromethoxy-4'-trifluoro-methyl-1,3-thiazole-5-carboxamide,
2,2-dichloro-N-[1-(4-chlorophenyl)-ethyl]-1-ethyl-3-methylcyclopropanecarboxamide,
2,6-dichloro-5-(methylthio)-4-pyrimidinyl thiocyanate,
2,6-dichloro-N-(4-trifluoromethylbenzyl)-benzamide,
2,6-dichloro-N-[[4-(trifluoromethyl)-phenyl]-methyl]-benzamide,
2-(2,3,3-triiodo-2-propenyl)-2H-tetrazole,
2-[(1-methylethyl)sulphonyl]-5-(trichloromethyl)-1,3,4-thiadiazole,
2-[[6-deoxy-4-O-(4-O-methyl-β-D-glycopyranosyl)-a-D-glucopyranosyl]-amino]-4-methoxy-1H-pyrrolo[2,3-d]pyrimidine-5-carbonitrile,
2-aminobutane,
2-bromo-2-(bromomethyl)-pentanedinitrile,
2-chloro-N-(2,3-dihydro-1,1,3-trimethyl-1H-inden-4-yl)-3-pyridine carboxamide,
2-chloro-N-(2,6-dimethylphenyl)-N-(isothiocyanatomethyl)-acetamide,
2-phenylphenol (OPP),
3,4-dichloro-1-[4-(difluoromethoxy)-phenyl]-1H-pyrrole-2,5-dione,
3,5-dichloro-N-[cyano-[(1-methyl-2-propynyl)-oxy]-methyl]-benzamide,
3-(1,1-dimethylpropyl-1-oxo-1H-indene-2-carbonitrile,
3-[2-(4-chlorophenyl)-5-ethoxy-3-isoxazolidinyl]-pyridine,
4-chloro-2-cyano-N,N-dimethyl-5-(4-methylphenyl)-1H-imidazole-1-sulphonamide,
4-methyl-tetrazolo[1,5-a]quinazolin-5(4H)-one,
8-(1,1-dimethylethyl)-N-ethyl-N-propyl-1,4-dioxaspiro[4,5]decane-2-methanamine,
8-hydroxyquinoline sulphate,
9H-xanthene-2-9-carboxylic-[(phenylamino)-carbonyl] hydrazide,
bis-(1-methylethyl)-3-methyl-4-[(3-methylbenzoyl)oxy]-2,5-thiophenedicarboxylate,
cis-1-(4-chlorophenyl)-2-(1H-1,2,4-triazol-1-yl)-cycloheptanol,
cis-4-[3-[4-(1,1-dimethylpropyl)-phenyl-2-methylpropyl]-2,6-dimethyl-morpholine hydrochloride,
ethyl [(4-chlorophenyl)-azo]-cyanoacetate,
potassium hydrogencarbonate,
methanetetrathiol sodium salt,
methyl 1-(2,3-dihydro-2,2-dimethyl-1H-inden-1-yl)-1H-imidazole-5-carboxylate,
methyl N-(2,6-dimethylphenyl)-N-(5-isoxazolylcarbonyl)-DL-alaninate,
methyl N-(chloroacetyl)-N-(2,6-dimethylphenyl)-DL-alaninate,
N-(2,3-dichloro-4-hydroxyphenyl)-1-methyl-cyclohexanecarboxamide,
N-(2,6-dimethylphenyl)-2-methoxy-N-(tetrahydro-2-oxo-3-furanyl)-acetamide,
N-(2,6-dimethylphenyl)-2-methoxy-N-(tetrahydro-2-oxo-3-thienyl)-acetamide,
N-(2-chloro-4-nitrophenyl)-4-methyl-3-nitro-benzenesulphonamide,
N-(4-cyclohexylphenyl)-1,4,5,6-tetrahydro-2-pyrimidinamine,
N-(4-hexylphenyl)-1,4,5,6-tetrahydro-2-pyrimidinamine,
N-(5-chloro-2-methylphenyl)-2-methoxy-N-(2-oxo-3-oxazolidinyl)-acetamide,
N-(6-methoxy)-3-pyridinyl)-cyclopropanecarboxamide,
N-[2,2,2-trichloro-1-[(chloroacetyl)-amino]-ethyl]-benzamide,
N-[3-chloro4,5-bis(2-propinyloxy)-phenyl]-N'-methoxy-methanimidamide,
N-formyl-N-hydroxy-DL-alanine mono-sodium salt,
O,O-diethyl [2-(dipropylamino)-2-oxoethyl]-ethylphosphoramidothioate,
O-methyl S-phenyl phenylpropylphosphoramidothioate,
S-methyl 1,2,3-benzothiadiazole-7-carbothioate,
spiro[2H]-1-benzopyran-2,1'(3'H)-isobenzofuran]-3'-one,
Bactericides:
  bromopol, dichlorophen, nitrapyrin, nickel dimethyldithiocarbamate, kasugamycin, octhilinone, furancarboxylic acid, oxytetracycline, probenazole, streptomycin, tecloftalam, copper sulphate and other copper preparations.
Insecticides/Acaricides/Nematicides:
  abamectin, acephate, acetamiprid, acrinathrin, alanycarb, aldicarb, aldoxycarb, alpha-cypermethrin, alphamethrin, amitraz, avermectin, AZ 60541, azadirachtin, aza-methiphos, azinphos A, azinphos M, azocyclotin,
  Bacillus popilliae, Bacillus sphaericus, Bacillus subtilis, Bacillus thuringiensis, baculoviruses, Beauveria bassiana, Beauveria tenella, bendiocarb, benfuracarb, bensultap, benzoximate, betacyfluthrin, bifenazate, bifenthrin, bioethanomethrin, biopermethrin, BPMC, bromophos A, bufencarb, buprofezin, butathiofos, butocarboxim, butylpyridaben,
  cadusafos, carbaryl, carbofuran, carbophenothion, carbosulfan, cartap, chloethocarb, chlorethoxyfos, chlorfenapyr, chlorfenvinphos, chlorfluazuron, chlormephos, chlorpyrifos, chlorpyrifos M, chlovaphorthrin, cis-resmethrin, cispermethrin, clocythrin, cloethocarb, clofentezine, cyanophos, cycloprene, cycloprothrin, cyfluthrin, cyhalothrin, cyhexatin, cypermethrin, cyromazine,
  deltamethrin, demeton M, demeton S, demeton-S-methyl, diafenthiuron, diazinon, dichlorvos, diflubenzuron, dimethoate, dimethylvinphos, diofenolan, disulfoton, docusat-sodium, dofenapyn, elfusilanate, emamectin, empenthrin, endosulfan, Entomopfthora spp., esfenvalerate, ethiofencarb, ethion, ethoprophos, etofenprox, etoxazole, etrimfos, fenamiphos, fenazaquin, fenbutatin oxide, fenitrothion, fenothiocarb, fenoxacrim, fenoxycarb, fenpropathrin, fenpyrad, fenpyrithrin, fenpyroximate, fenvalerate, fipronil, fluazinam, fluazuron, flubrocythrinate, flucycloxuron, flucythrinate, flufenoxuron, flutenzine, fluvalinate, fonophos, fosmethilan, fosthiazate, fubfenprox, furathiocarb, granulosis viruses, halofenozide, HCH, heptenophos, hexaflumuron, hexythiazox, hydroprene, imidacloprid, isazofos, isofenphos, isoxathion, ivermectin, nuclear polyhedrosis viruses, lambda-cyhalothrin, lufenuron, malathion, mecarbam, metaldehyde, methamidophos, Metharhizium anisopliae, Metharhizium flavoviride, methidathion, methiocarb, methomyl, methoxyfenozide, metolcarb, metoxadiazone, mevinphos, milbemectin, monocrotophos, naled, nitenpyram, nithiazine, novaluron, omethoate, oxamyl, oxydemethon M, Paecilomyces fumosoroseus, parathion A, parathion M, permethrin, phenthoate, phorate, phosalone, phosmet, phosphamidon, phoxim, pirimicarb, pirimiphos A, pirimiphos M, profenofos, promecarb, propoxur, prothiofos, prothoate, pymetrozine, pyraclofos, pyresmethrin, pyrethrum, pyridaben, pyridathion, pyrimidifen, pyriproxyfen, quinalphos, ribavirin, salithion, sebufos, silafluofen, spinosad, sulfotep, sulprofos, tau-fluvalinate, tebufenozide, tebufenpyrad, tebupirimiphos, teflubenzuron, tefluthrin, temephos, temivinphos, terbufos, tetrachlorvinphos, theta-cypermethrin, thiacloprid, thiamethoxam, thiapronil, thiatriphos, thiocyclam hydrogen oxalate, thiodicarb, thiofanox, thuringiensin, tralocythrin, tralomethrin, triarathene, triazamate, triazophos, triazuron, trichlophenidine, trichlorfon, triflumuron, trimethacarb, vamidothion, vaniliprole, *Verticillium lecanii*, YI50302, zeta-cypermethrin, zolaprofos, (1R-cis)-[5-(phenylmethyl)-3-furanyl]-methyl 3-[(dihydro-2-oxo-3(2H)-furanylidene)-methyl]-2,2-dimethylcyclopropanecarboxylate, (3-phenoxyphenyl)-methyl 2,2,3,3-tetramethylcyclopropanecarboxylate, 1-[(2-chloro-5-thiazolyl)methyl]tetrahydro-3,5-dimethyl-N-nitro-1,3,5-triazine-2(1H)-imine, 2-(2-chloro-6-fluorophenyl)-4-[4-(1,1-dimethylethyl)phenyl]4,5-dihydro-oxazole, 2-(acetlyoxy)-3-dodecyl-1,4-naphthalenidione, 2-chloro-N-[[[4-(1-phenylethoxy)-phenyl]-amino]-carbonyl]-benzamide, 2-chloro-N-[[[4-(2,2-dichloro-1,1-difluoroethoxy)-phenyl]-amino]-carbonyl]-benzamide, 3-methylphenyl propylcarbamate, 4-[4-(4-ethoxyphenyl)4-methylpentyl]-1-fluoro-2-phenoxybenzene, 4-chloro-2-(1,1-dimethylethyl)-5-[[2-(2,6-dimethyl4-phenoxyphenoxy)ethyl]thio]-3(2H)-pyridazinone, 4-chloro-2-(2-chloro-2-methylpropyl)-5-[(6-iodo-3-pyridinyl)methoxy]-3(2H)-pyridazinone, 4-chloro-5-[(6-chloro-3-pyridinyl)methoxy]-2-(3,4-dichlorophenyl)-3(2H)-pyridazinone,

*Bacillus thuringiensis* strain EG-2348, 2-benzoyl-1-(1,1-dimethylethyl)-hydrazinobenzoic acid, 2,2-dimethyl-3-(2,4-dichlorophenyl)-2-oxo-1-oxaspiro[4.5]dec-3-en-4-yl butanoate,

[3-[(6-chloro-3-pyridinyl)methyl]-2-thiazolidinylidene]-cyanamide, dihydro-2-(nitromethylene)-2H-1,3-thiazine-3(4H)-carboxaldehyde, ethyl [2-[[1,6-dihydro-6-oxo-1-(phenylmethyl)-4-pyridazinyl]oxy]ethyl]-carbamate, N-(3,4,4-trifluoro-1-oxo-3-butenyl)-glycine, N-(4-chlorophenyl)-3-(4-(difluoromethoxy)phenyl]-4,5-dihydro-4-phenyl-1H-pyrazole-1-carboxamide, N-[(2-chloro-5-thiazolyl)methyl]-N'-methyl-N"-nitro-guanidine, N-methyl-N'-(1-methyl-2-propenyl)-1,2-hydrazinedicarbothioamide, N-methyl-N'-2-propenyl-1,2-hydrazinedicarbothioamide, O,O-diethyl [2-(dipropylamino)-2-oxoethyl]-ethylphosphoramidothioate.

It is also possible to admix other known active compounds, such as herbicides, or fertilizers and growth regulators.

The active compounds can be used as such or in the form of their formulations or the use forms prepared therefrom, such as ready-to-use solutions, suspensions, wettable powders, pastes, soluble powders, dusts and granules. They are used in the customary manner, for example by pouring, spraying, atomizing, spreading, dusting, foaming, brushing on and the like. It is further possible to apply the active compounds by the ultra-low volume method or to inject the active compound formulation, or the active compound itself, into the soil. The seed of the plants can also be treated.

When using the active compounds according to the invention as fungicides, the application rates can be varied within a relatively wide range, depending on the type of application. In the treatment of parts of plants, the application rates of active compounds are generally between 0.1 and 10 000 g/ha, preferably between 10 and 1000 g/ha. In the treatment of seed, the application rates of active compounds are generally between 0.001 and 50 g per kilogram of seed, preferably between 0.01 and 10 g per kilogram of seed. In the treatment of the soil, the application rates of active compound are generally between 0.1 and 10000 g/ha, preferably between 1 and 5000 g/ha.

The compositions used for protecting industrial materials comprise the active compounds generally in an amount of from 1 to 95% by weight, preferably from 10 to 75% by weight.

The use concentrations of the active compounds according to the invention depend on the species and the occurrence of the microorganisms to be controlled, and on the composition of the material to be protected. The optimum rate of application can be determined by test series. The use concentrations are generally in the range from 0.001 to 5% by weight, preferably from 0.05 to 1.0% by weight, based on the material to be protected.

The activity and the activity spectrum of the active compounds to be used according to the invention in the protection of materials, or the compositions, concentrates or quite generally formulations preparable therefrom, can be increased by adding, if appropriate, other antimicrobially active compounds, fungicides, bactericides, herbicides, insecticides or other active compounds for broadening the activity spectrum or obtaining particular effects, such as, for example, the additional protection against insects. These mixtures may have a broader activity spectrum than the compounds according to the invention.

The preparation and use of active compounds according to the invention are illustrated by the following examples.

The sulphonyl-triazole derivatives of the formula (I) according to the invention can also be used for treating transgenic plants. In combination with the substances formed by expression, it is possible for synergistic effects to occur.

PREPARATION EXAMPLES

Example 1

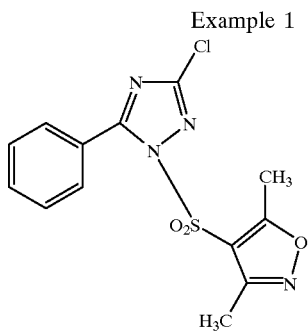

At room temperature, a solution of 1.8 g (10 mmol) of 3-phenyl-5-chloro-1,2,4-triazole in 40 ml of acetonitrile is mixed with stirring with 1.4 g (10 mmol) of potassium carbonate and then stirred at room temperature for 10 minutes. 2.0 g (10 mmol) of 3,5-dimethyl-isoxazole4-sulphonyl chloride are then added, and the mixture is stirred at room temperature for another 20 hours. For work-up, the reaction mixture is poured into 150 ml of water. The resulting mixture is extracted twice with in each case 40 ml of methylene chloride. The combined organic phases are dried over sodium sulphate and concentrated under reduced pressure. The residue that remains is chromatographed on silica gel using the mobile phase methylene chloride. This gives 1.7 g (50% of theory) of 3-phenyl-5-chloro-2-(3,4-dimethyl-isoxazole-4-sulphonyl)-1,2,4-triazole in the form of a solid of melting point 70 to 74° C. log p: 3.67

The sulphonyltriazole derivatives of the formula (I) listed in the table below are also prepared by the method given above.

TABLE 1

(I)

| Ex. No. | Hal | $R^1$ | $R^2$ | Melting point in ° C. |
|---|---|---|---|---|
| 2 | Cl | ⌬ (phenyl) | 2,4-dimethyl-5-nitrophenyl | 136–140 |
| 3 | Cl | H | 3,4-dimethyl-isoxazol-5-yl | 129–133 |
| 4 | Cl | H | 3-amino-4-methyl-isoxazol-5-yl | 200–203 |
| 5 | Cl | ⌬ (phenyl) | 2,5-dichloro-3-methylthiophen-4-yl | 91–94 |

TABLE 1-continued
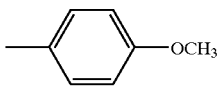
(I)
| Ex. No. | Hal | R¹ | R² | Melting point in ° C. |
|---|---|---|---|---|
| 6 | Cl | 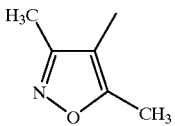 4-methoxyphenyl | 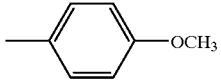 3,5-dimethylisoxazol-4-yl | 65 |
| 7 | Cl | 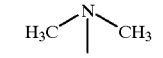 4-methoxyphenyl |  N(CH₃)₂ | 66 |
| 8 | Cl | 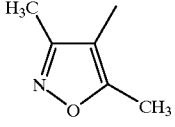 4-chlorophenyl | 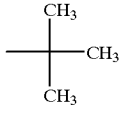 3,5-dimethylisoxazol-4-yl | 131–132 |
| 9 | Cl | 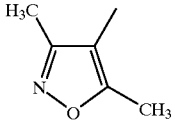 tert-butyl | 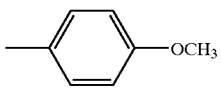 3,5-dimethylisoxazol-4-yl | 83–84 |
| 10 | Cl | 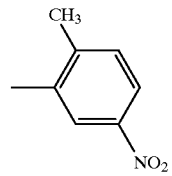 4-methoxyphenyl |  3,4-dimethyl-6-nitrophenyl | 90–92 |
| 11 | Cl | 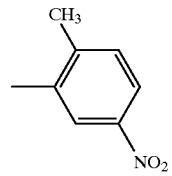 4-chlorophenyl | 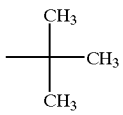 3,4-dimethyl-6-nitrophenyl | 186–188 |
| 12 | Cl | 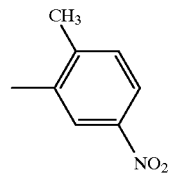 tert-butyl | 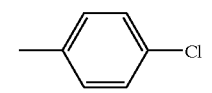 3,4-dimethyl-6-nitrophenyl | 87–88 |
| 13 | Cl | 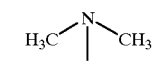 4-chlorophenyl | H₃C-N(CH₃) | 122–126 |

TABLE 1-continued
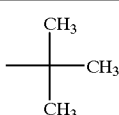
(I)
| Ex. No. | Hal | R¹ | R² | Melting point in °C. |
|---|---|---|---|---|
| 14 | Cl | 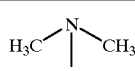 | 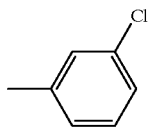 | logP: 3.05* |
| 15 | Cl | 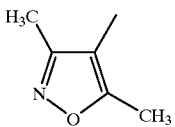 | 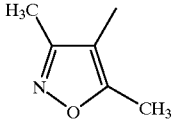 | 99–100 |
| 16 | Br | —CH₃ | 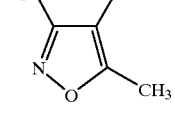 | 60–64 |
| 17 | Br | —CH₃ | 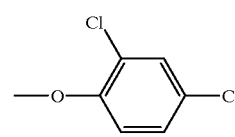 | 149–152 |
| 18 | Cl | 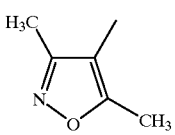 | 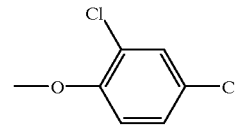 | 147–150 |
| 19 | Cl | 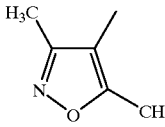 | 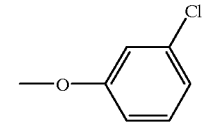 | 139–143 (Isomer of 18) |
| 20 | Cl | 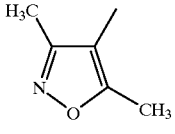 | 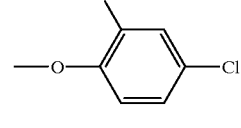 | 103–105 |
| 21 | Cl |  | 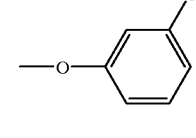 | logP: 3.73* |
| 22 | Cl |  | | logP: 3.70* |

TABLE 1-continued
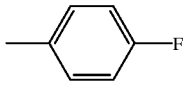
(I)
| Ex. No. | Hal | R¹ | R² | Melting point in °C. |
|---|---|---|---|---|
| 23 | Cl | 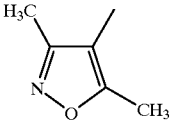 | 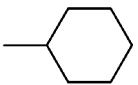 | 95–99 |
| 24 | Cl | 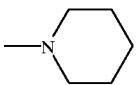 | 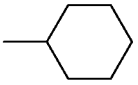 | 44–45 |
| 25 | Cl | 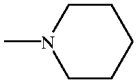 | 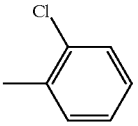 | 73–76 (Isomer of 24) |
| 26 | Cl | 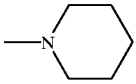 | 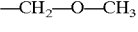 | logP: 3.76* |
| 27 | Cl | —CH₂—O—CH₃ | 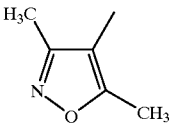 | 45–47 |
| 28 | Cl | —CH₂—O—CH₃ | 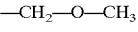 | 136–138 |
| 29 | Cl | 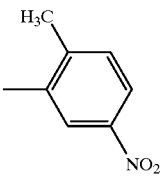 | 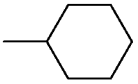 | 63–65 |
| 30 | Cl | 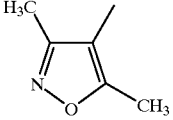 | 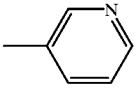 | 127–129 |
| 31 | Cl | 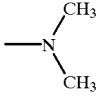 | 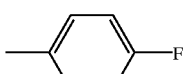 | 138–142 |

TABLE 1-continued (I)

| Ex. No. | Hal | R¹ | R² | Melting point in °C. |
|---|---|---|---|---|
| 32 | Cl | 2,4-dichlorophenyl | 3,4-dimethyl-5-methylisoxazol-yl (3,4-dimethylisoxazol-5-yl) | 180–183 |
| 33 | Cl | —C(O)—NH—C(CH₃)₃ | piperidin-1-yl | 84–89 |
| 34 | Cl | —C(O)—NH—C(CH₃)₃ | —N(CH₃)₂ | 126–128 |
| 35 | Cl | pyridin-3-yl | 3,4-dimethylisoxazol-5-yl | logP: 2.18* |
| 36 | Cl | piperidin-1-yl | —N(CH₃)₂ | 78–84 |
| 37 | Cl | 2-chlorophenyl | 3,4-dimethylisoxazol-5-yl | 120–122 |
| 38 | Cl | pyridin-3-yl | piperidin-1-yl | 84–89 |
| 39 | Cl | cyclohexyl | 2-methyl-4-nitro-phenyl (with CH₃ and NO₂) | 135–138 |
| 40 | Cl | 4-fluorophenyl | piperidin-1-yl | 98–99 |
| 41 | Cl | CH₂—O—CH₃ | —N(CH₃)₂ | logP: 1.83* |

TABLE 1-continued

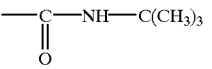

(I)

| Ex. No. | Hal | R¹ | R² | Melting point in ° C. |
|---|---|---|---|---|
| 42 | Cl | 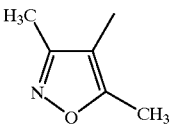 | 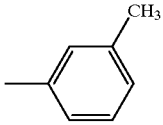 | 96–98 |
| 43 | Cl | 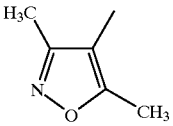 | 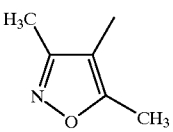 | logP: 4.06* |
| 44 | Cl | —CH₃ | | logP: 2.61* |
| 45 | Cl | —CH₃ | 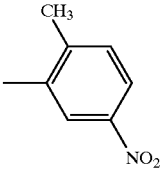 | logP: 3.03* |
| 46 | Cl | —CH₃ |  | logP: 1.81* |

*The logP values were determined in accordance with EEC directive 79/831 Annex V. A 8 by HPLC (gradient method; acetonitrile/0.1% aqueous phosphoric acid).

Use Examples

Example A

Phytophthora Test (Tomato)/Protective

Solvent: 47 parts by weight of acetone
Emulsifier: 3 parts by weight of alkyl-aryl polyglycol ether
To produce a suitable preparation of active compound, 1 part by weight of active compound is mixed with the stated amounts of solvent and emulsifier and the concentrate is diluted to the desired concentration.

To test for protective activity, young plants are sprayed with the preparation of active compound at the stated application rate. After the spray coating has dried on, the plants are inoculated with an aqueous spore suspension of Phytophthora infestans. The plants are then placed in an incubation cabin at about 20° C. and 100% relative atmospheric humidity.

Evaluation is carried out 3 days after the inoculation. 0% means an efficacy which corresponds to that of the control, whereas an efficacy of 100% means that no infection is observed.

Active compound, application rates and test results are shown in the table below.

TABLE A

Phytophthora test (tomato)/protective

| Active compound | Application rate of active compound in g/ha | Efficacy in % |
|---|---|---|
| According to the invention: | | |
| (1) 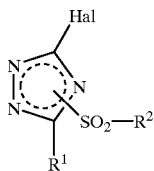 | 50 | 97 |

What is claimed is:

1. A sulphonyltriazole derivative of the formula

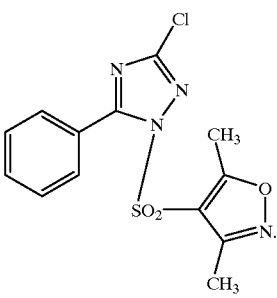

in which

Hal represents fluorine, chlorine or bromine, $R^1$ represents hydrogen, methyl, ethyl, n-propyl, isopropyl, n-butyl, sec-butyl, iso-butyl or tert-butyl, or represents alkoxyalkyl having 1 to 4 carbon atoms in the alkoxy moiety and 1 to 4 carbon atoms in the alkyl moiety, or represents cycloalkyl having 3 to 7 carbon atoms, or represents alkylaminocarbonyl having 1 to 4 carbon atoms in the alkyl moiety, or $R^1$ represents phenyl which may be mono- to trisubstituted by identical or different substituents from the group consisting of fluorine, chlorine, bromine, nitro, methyl, ethyl, n- or i-propyl, n-, i-, s- or t-butyl, methoxy, ethoxy, n- or i-propoxy, methylthio, ethylthio, n- or i-propylthio, trifluoromethyl, trifluoroethyl, difluoromethoxy, trifluoromethoxy, difluorochloromethoxy, trifluoroethoxy, cyano, cyclopropyl, cyclopentyl and cyclohexyl, or $R^1$ represents phenoxy which may be mono- to trisubstituted by identical or different substituents from the group consisting of fluorine, chlorine, bromine, nitro, methyl, ethyl, n- or i-propyl, n-, i-, s- or t-butyl, methoxy, ethoxy, n- or i-propoxy, methylthio, ethylthio, n- or i-propylthio, trifluoromethyl, trifluoroethyl, difluoromethoxy, trifluoromethoxy, difluorochloromethoxy, trifluoroethoxy, cyano, cyclopropyl, cyclopentyl and cyclohexyl, and $R^2$ represents isoxazolyl which may be mono- or disubstituted by identical or different substituents from the group consisting of fluorine, chlorine, bromine, cyano, nitro, amino, hydroxyl, carbamoyl, methyl, ethyl, n- or i-propyl, n-, i-, s-, or t-butyl, cyclopropyl, methoxy, ethoxy, n- or i-propoxy, trifluoromethyl, trifluoroethyl, difluoromethoxy, trifluoromethoxy, acetyl, propionyl, methoxycarbonyl, ethoxycarbonyl, hydroximinomethyl, hydroxyiminoethyl, methoximinomethyl, ethoximinomethyl, methoximinoethyl and ethoximinoethyl.

2. A composition for controlling undesirable microorganisms, comprising an effective amount of a sulphonyltriazole derivative of the formula (I) according to claim 1 and an inert diluent.

3. A method for controlling undesired microorganisms, comprising the step of apply an effective amount of a sulphonyltriazole derivative of the formula (I) according to claim 1 to the microorganisms and/or their habitat.

4. Sulphonyltriazole derivative according to claim 1, characterized by the formula 5. A method according to claim 3, wherein the microorganisms are selected from the group consisting of bacteria, fungi, yeasts, algae and slime organisms.

6. A sulphonyltriazole derivative according to claim 1, wherein $R^1$ represents hydrogen, methyl, ethyl, n-propyl, iso-propyl, n-butyl, sec-butyl, iso-butyl or tert-butyl, or represents alkoxyalkyl having 1 to 2 carbon atoms in the alkoxy moiety and 1 to 2 carbon atoms in the alkyl moiety, or represents cyclopropyl, cyclopentyl, cyclohexyl, or represents alkylaminocarbonyl having 1 to 4 carbon atoms in the alkyl moiety.

7. A sulphonyltriazole derivative according to claim 1, wherein $R^1$ represents phenyl which may be mono- to trisubstituted by identical or different substituents from the group consisting of fluorine, chlorine, bromine, nitro, methyl, ethyl, n- or i-propyl, n-, i-, s- or t-butyl, methoxy, ethoxy, n- or i-propoxy, methylthio, ethylthio, n- or i-propylthio, trifluoromethyl, trifluoroethyl, difluoromethoxy, trifluoromethoxy, difluorochloromethoxy, trifluoroethoxy, cyano, cyclopropyl, cyclopentyl and cyclohexyl.

8. A sulphonyltriazole derivative according to claim 1, wherein $R^1$ represents phenoxy which may be mono- to trisubstituted by identical or different substituents from the group consisting of fluorine, chlorine, bromine, nitro, methyl, ethyl, n- or i-propyl, n-, i-, s- or t-butyl, methoxy, ethoxy, n- or i-propoxy, methylthio, ethylthio, n- or i-propylthio, trifluoromethyl, trifluoroethyl, difluoromethoxy, trifluoromethoxy, difluorochloromethoxy, trifluoroethoxy, cyano, cyclopropyl, cyclopentyl and cyclohexyl.

9. A sulphonyltriazole derivative according to claim 1, wherein $R^2$ represents isoxazolyl which is disubstituted by identical or different substituents from the group consisting of fluorine, chlorine, bromine, cyano, nitro, amino, hydroxyl, carbamoyl, methyl, ethyl, n- or i-propyl, n-, i-, s-, or t-butyl, cyclopropyl, methoxy, ethoxy, n- or i-propoxy, trifluoromethyl, trifluoroethyl, difluoromethoxy, trifluoromethoxy, acetyl, propionyl, methoxycarbonyl, ethoxycarbonyl, hydroximinomethyl, hydroxyiminoethyl, methoximinomethyl, ethoximinomethyl, methoximinoethyl and ethoximinoethyl.

* * * * *